(12) United States Patent
Nipanikar et al.

(10) Patent No.: US 11,179,433 B2
(45) Date of Patent: Nov. 23, 2021

(54) MOUTH FRESHENER

(71) Applicant: ARI HEALTHCARE PVT. LTD., Maharashtra (IN)

(72) Inventors: Sanjay Nipanikar, Maharashtra (IN); Anisha Kanjilal, Maharashtra (IN); Sanjeevan Kanjilal, Maharashtra (IN)

(73) Assignee: ARI HEALTHCARE PVT. LTD., Maharashtra (IN)

( * ) Notice: Subject to any disclaimer, the term of this patent is extended or adjusted under 35 U.S.C. 154(b) by 589 days.

(21) Appl. No.: 15/532,532

(22) PCT Filed: Dec. 11, 2015

(86) PCT No.: PCT/IB2015/059544
§ 371 (c)(1),
(2) Date: Jun. 2, 2017

(87) PCT Pub. No.: WO2016/092518
PCT Pub. Date: Jun. 16, 2016

(65) Prior Publication Data
US 2017/0326196 A1  Nov. 16, 2017

(30) Foreign Application Priority Data

Dec. 12, 2014 (IN) .......................... 4002/MUM/2014

(51) Int. Cl.
| | |
|---|---|
| *A61K 36/9066* | (2006.01) |
| *A61K 36/67* | (2006.01) |
| *A61K 36/534* | (2006.01) |
| *A61K 8/9789* | (2017.01) |
| *A61K 8/9794* | (2017.01) |
| *A61Q 11/00* | (2006.01) |

(52) U.S. Cl.
CPC ........ *A61K 36/9066* (2013.01); *A61K 8/9789* (2017.08); *A61K 8/9794* (2017.08); *A61K 36/534* (2013.01); *A61K 36/67* (2013.01); *A61Q 11/00* (2013.01); *A61K 2300/00* (2013.01)

(58) Field of Classification Search
None
See application file for complete search history.

(56) References Cited

U.S. PATENT DOCUMENTS

| | | | | |
|---|---|---|---|---|
| 2006/0270715 | A1* | 11/2006 | Singh ................... | A61K 9/2009 514/355 |
| 2006/0286201 | A1* | 12/2006 | Jani ......................... | A23G 4/18 426/5 |
| 2007/0092553 | A1* | 4/2007 | Tengler ................ | A61K 9/0056 424/440 |
| 2007/0116652 | A1 | 5/2007 | Kamath et al. | |
| 2010/0247593 | A1* | 9/2010 | Wikberg .............. | A61K 31/366 424/422 |

OTHER PUBLICATIONS

International Preliminary Report on Patentability and Written Opinion of the International Searching Authority of PCT/IB2015/059544 dated Jun. 13, 2017.
MH5/289A: Maajoon Falaasfa Deegar; Knowledge known since: 200 years; (Source: www.tkdl.res.in).
MH2/278X: Dawa Baraae Ghazeedadi-e-Sag; Knowledge known since: 1000 years; (Source: www.tkdl.res.in).
International Search Report of PCT/IB2015/059544, dated Mar. 21, 2016.
"An open label, interventional, single center, prospective clinical study to evaluate efficacy and safety of 'AHPL/AYTAB/1514' in patients suffering from halitosis." Clinical Trials Registry—India, National Institute of Medical Statistics (Indian Council of Medical Research), REF/2015/07/009483, CTRI Website URL—http://ctri.nic.in, retrieved on May 19, 2017, 4 pages.

\* cited by examiner

*Primary Examiner* — Terry A McKelvey
*Assistant Examiner* — Catheryne Chen
(74) *Attorney, Agent, or Firm* — Collard & Roe, P.C.

(57) ABSTRACT

The present disclosure envisages a mouth freshener composition comprising the extracts of *Curcuma longa*, *Piper longum* and *Mentha arvensis*. Further, the composition comprises at least one diluent, at least one sweetening agent, at least one binder, at least one preservative, at least one pharmaceutically acceptable fluid medium, at least one pharmaceutically acceptable flavoring agent, at least one pharmaceutically acceptable lubricant, optionally at least one pharmaceutically acceptable disintegrant, at least one pharmaceutically acceptable glidant, at least one pharmaceutically acceptable film forming agent, at least one pharmaceutically acceptable plasticizer. The present disclosure also envisages a process for preparing the mouth freshener composition. The mouth freshener composition alleviates halitosis, common cold, cough, sore throat and the symptoms of bronchitis. It also acts as a rejuvenator and Immunomodulator on prolonged use.

10 Claims, No Drawings

MOUTH FRESHENER

CROSS REFERENCE TO RELATED APPLICATIONS

This application is the National Stage of PCT/IB2015/059544 filed on Dec. 11, 2015, which claims priority under 35 U.S.C. § 119 of Indian Application No. 4002/MUM/2014 filed on Dec. 12, 2014, the disclosures of which are incorporated by reference. The international application under PCT article 21(2) was published in English.

FIELD

The present disclosure relates to the field of mouth fresheners.

BACKGROUND

Halitosis or bad breath is the unpleasant odour majorly originating from the oral cavity. This foul odour originating from the mouth is also called intra-oral halitosis, oral malodour or oral halitosis. Halitosis is caused by a variety of reasons including, but not limited to, periodontal disease, bacterial coating of the tongue, systemic disorders and consumption of different types of food. The primary cause of halitosis is the release of volatile sulphur compounds (VSCs). This oral malodour is caused by bacteria like *Fusobacterium nucleatum, Prevotella intermedia, Tannerella forsythensis, Porphyromonas gingivalis* and *Treponema denticola*.

A primary treatment for halitosis includes proper oral hygiene, i.e. brushing, flossing, and gargling. Other treatments include the mechanical approach of scaling and root planning of the root pockets and tongue cleaning, the chemical approach of using a mouthwash to reinforce mouth cleaning after eating or drinking. Many people use deodorant-type mouth rinses and mints which provide only short-term and masking effects instead of using a proper diagnostic method and etiologic care to manage bad breath. Typically, these mouthwashes mostly contain chlorhexidine, which decreases the formation of VSCs. However, long term use of chlorhexidine impairs the taste and irritates the soft tissue in the mouth.

Also, halitosis has important socio-economic consequences and is considered as a social stigma in an ever-growing sensitive society.

Accordingly, there exists a need to develop a solution to overcome the above mentioned drawbacks which has minimal side effects.

OBJECTS

Some of the objects of the present disclosure, which at least one embodiment herein satisfies, are as follows:

It is an object of the present disclosure to ameliorate one or more problems of the prior art or to at least provide a useful alternative.

It is an object of the present disclosure to provide a mouth freshener composition which is safe and nontoxic and with minimal side effects.

It is another object of the present disclosure is to provide a mouth freshener composition which can be administered orally.

It is another object of the present disclosure is to provide a mouth freshener composition which is effective in alleviating halitosis.

It is yet another object of the present disclosure to provide a mouth freshener composition which is effective in alleviating the symptoms of common cold, cough and sore throat.

It is still another object of the present disclosure to provide a mouth freshener composition which acts as an immunomodulator and rejuvenator.

It is yet another object of the present disclosure to provide a process for producing the mouth freshener composition.

Other objects and advantages of the present disclosure will be more apparent from the following description, which is not intended to limit the scope of the present disclosure.

SUMMARY

The present disclosure envisages a mouth freshener composition, as a rejuvenator and as an immunomodulator, comprising the extracts of *Curcuma longa, Piper longum* and *Mentha arvensis*. Further, the composition can also comprise at least one diluent, at least one sweetening agent, at least one binder, at least one preservative, at least one pharmaceutically acceptable fluid medium, at least one pharmaceutically acceptable flavoring agent, optionally at least one pharmaceutically acceptable disintegrant, at least one pharmaceutically acceptable lubricant, at least one pharmaceutically acceptable glidant, at least one pharmaceutically acceptable coating material, at least one pharmaceutically acceptable film forming polymer and at least one pharmaceutically acceptable plasticizer.

The present disclosure also envisages a process for preparing the mouth freshener composition. The process involves sifting, individually, the sweetener, diluent and ethyl acetate extract of *Curcuma longa*, hydroalcoholic extract of *Piper longum* and hydroalcoholic extract of *Mentha arvensis* through a sieve. The sweetener is then geometrically mixed with a diluent followed by adding ethyl acetate extract of *Curcuma longa*, hydroalcoholic extract of *Piper longum* and hydroalcoholic extract of *Mentha arvensis* to form a first homogenised blend. Separately, Isopropyl alcohol and purified water are mixed in a predetermined amount to form a first mixture. At least one binder and at least one preservative are added to the first mixture and dissolved to form a second mixture. The second mixture is blended with the first blend to form a second blend which is granulated to form granules, followed by drying at a temperature ranging from 40° C. to 70° C. till loss on drying is achieved between 1.5 to 4% followed by sifting to form dried granules.

The flavouring agents and glidant are then sifted through a sieve (aperture size of 425 micron) to obtain a third mixture. Then the third mixture is mixed with dried and sized granules to form a fourth mixture. Separately the lubricant is sifted through a sieve (aperture size of 250 micron) and mixed with the fourth mixture. This fourth mixture is then compressed to form tablets.

The compressed tablets are coated with a polymeric coating film to form the mouth freshener tablet of the present disclosure.

DETAILED DESCRIPTION

Offensive breath is a considerable problem pertaining to oral hygiene, also known as halitosis. This odour is formed by decomposition of residues of food and dead cells of the mucous membrane by microorganisms. Since bad breath seriously impedes social interaction and affects the mental health, those affected by it have a great interest in remedying or preventing it.

Accordingly, there exists a need to develop a solution for overcoming the above mentioned drawbacks which is devoid of any side effects.

The inventors of the present disclosure envisaged a mouth freshener composition comprising at least three plant based materials. The mouth freshener composition as disclosed in the present disclosure is effective in alleviating halitosis with minimal side effects.

In accordance with one aspect of the present disclosure there is provided a mouth freshener composition comprising:
- i. *Curcuma longa;*
- ii. *Piper longum;*
- iii. *Mentha arvensis;* and
- iv. at least one pharmaceutically acceptable excipient.

*Curcuma longa* is native to the Indian sub-continent, but also grows in Pakistan, Sri-Lanka and Bangladesh. *Piper longum* is also native to the Indian sub-continent, but is known to grow in the Asian continent. *Mentha arvensis* is native to the Indian sub-continent and also grows in European and Asian continents.

The scope of the present disclosure is not only limited to *Curcuma longa, Piper longum, Mentha arvensis* and products derived therefrom but also extends to botanically closely related plants specially belonging to the same family, preferably belonging to the same genus still preferably belonging to the same species having substantially similar phenotypic and genotypic characteristics.

The plant extracts maybe derived from bark, roots, tubers, stolons, rhizome, leaves, seeds, fruits, stems and flowers, preferably, rhizomes of *Curcuma longa*, fruit of *Piper longum* and leaves of *Mentha arvensis*.

The extracts of *Curcuma longa, Mentha arvensis* and *Piper longum* may be taken in the form of a powder obtained by direct micronization of the plant material. Alternatively, the extracts maybe in the form of a solid or a semi-solid or a liquid. Typically, the extracts are selected from the group that include but is not limited to alcoholic, hydroalcoholic, aqueous, ether, ester, ethyl acetate, acetone and hexane extract. Typically, the extracts are prepared by using techniques that includes but are not limited to percolation, decoction, maceration, soxhlet extraction and supercritical fluid extraction.

In an embodiment of the present disclosure, the mouth freshener composition comprises:
- i) ethyl acetate extract of *Curcuma longa* in an amount ranging from 0.05 to 85.0% with respect to the total weight of the composition;
  - wherein said extract of *Curcuma longa* has at least 5% of curcuminoids;
- ii) hydroalcoholic extract of *Piper longum* in an amount ranging from 0.005 to 5.0% with respect to the total weight of the composition;
  - wherein said extract of *Piper longum* has at least 1% of piperine;
- iii) hydroalcoholic extract of *Mentha arvensis* in an amount ranging from 0.005 to 5.0% with respect to the total weight of the composition;
  - wherein said extract of *Mentha arvensis* has at least 0.5% of total volatile oil;
- iv) at least one diluent in an amount ranging from 0.1 to 90.0% with respect to the total weight of the composition;
- v) at least one sweetening agent in an amount ranging from 1.0 to 2.0% with respect to the total weight of the composition;
- vi) at least one binder in an amount ranging from 1.5 to 3.0% with respect to the total weight of the composition;
- vii) at least one preservative in an amount ranging from 0.015 to 0.3% with respect to the total weight of the composition;
- viii) at least one pharmaceutically acceptable flavouring agent in an amount ranging from 0.35 to 6.0% with respect to the total weight of the composition;
- ix) optionally at least one pharmaceutically acceptable disintegrant in an amount ranging from 4.0 to 6.0% with respect to the total weight of the composition;
- x) at least one pharmaceutically acceptable lubricant in an amount ranging from 0.5 to 1.2% with respect to the total weight of the composition;
- xi) at least one pharmaceutically acceptable glidant in an amount ranging from 0.5 to 1.2% with respect to the total weight of the composition;
- xii) at least one pharmaceutically acceptable film forming agent in an amount ranging from 0.8 to 1.2% with respect to the total weight of the composition; and
- xiii) at least one pharmaceutically acceptable plasticizer in an amount ranging from 0.2 to 0.3% with respect to the total weight of the composition.

The mouth freshener composition of the present disclosure is non-toxic and has no severe side effects. Moreover, it also has good stability and is suitable for mass production.

The composition of the present disclosure possesses anti-bacterial, anti-fungal and anti-microbial properties and helps in alleviating the symptoms of halitosis, common cold, cough, sore throat and bronchitis. Further, on a continuous long term use, the mouth freshener composition of the present disclosure is also effective as a rejuvenator and as an immunomodulator.

Typically, the proportion of *Curcuma longa* to *Piper longum* to *Mentha arvensis* as used in the present disclosure is 20:1:1.

Typically, the diluent can be selected from the group consisting of, but not limited to, mannitol, sucralose, lactose, microcrystalline cellulose, dextrin, maltitol and isomalt, wherein the amount of the diluent ranges from 0.1 to 90.0% with respect to the total weight of the composition.

Typically, the sweetening agent can be selected from the group consisting of, but not limited to, sucralose, acesulfame potassium, neotame, saccharine sodium, sucrose, aspartame *stevia* extracts, steviol glycoside and any sweetener derived from *stevia* plant, wherein the amount of the sweetening agent ranges from 1.0 to 2.0% with respect to the total weight of the composition.

Typically, the binder can be selected from the group consisting of, but not limited to, povidone, hydroxylpropyl methylcellulose, ethylcellulose, hydroxypropyl cellulose, starch, gum acacia, alginate, and carboxymethyl cellulose sodium and carboxymethyl cellulose calcium, wherein the amount of the binder ranges from 1.5 to 3.0% with respect to the total weight of the composition.

Typically, the preservative can be selected from the group consisting of, but not limited to, methylparaben, propylparaben, ethyl paraben, butyl paraben and sodium benzoate, wherein the amount of the preservative ranges from 0.015 to 0.30% with respect to the total weight of the composition.

Typically, the fluid medium can be selected from the group consisting of, but not limited to, isopropyl alcohol, dichloromethane and ethanol.

Typically, the flavouring agent can be selected from the group consisting of, but not limited to, menthol, peppermint, lemon, fennel, honey, mix fruit, orange, pineapple, raspberry, strawberry, vanilla, chocolate and cardamom, wherein the amount of the flavouring agent ranges from 0.35 to 6.0% with respect to the total weight of the composition.

Typically, the lubricant can be selected from the group consisting of, but not limited to, magnesium stearate, calcium stearate, stearic acid, glyceryl palmitostearate, colloidal anhydrous silica, sodium stearylfumarate and glyceryl monostearate, wherein the amount of the lubricant ranges from 0.50 to 1.2% with respect to the total weight of the composition.

Typically, the pharmaceutically acceptable disintegrants can be selected from the group consisting of, but not limited to, crospovidone, croscarmellose sodium, sodium starch glycolate, starch and colloidal anhydrous silica, wherein the amount of the pharmaceutically acceptable disintegrants ranges from 4.0 to 6.0% with respect to the total weight of the composition.

Typically, the pharmaceutically acceptable glidants can be, but not limited to, colloidal anhydrous silica, wherein the amount of the glidant ranges from 0.5 to 1.2% with respect to the total weight of the composition.

Typically, the pharmaceutically acceptable film forming agents can be selected from the group consisting of, but not limited to, hydroxylpropyl methylcellulose, ethylcellulose, hydroxylpropyl cellulose, povidone and polyvinyl alcohol, wherein the amount of the pharmaceutically acceptable film forming agents ranges from 0.8 to 1.2% with respect to the total weight of the composition.

Typically, the pharmaceutically acceptable plasticizer agents can be selected from the group consisting of, but not limited to, triacetin, glycerin, propylene glycol, polyethylene glycol and tweens, wherein the amount of the pharmaceutically acceptable plasticizer ranges from 0.2 to 0.3% with respect to the total weight of the composition.

In a preferred embodiment of the present disclosure, there is provided a process for preparing the mouth freshener composition in the form of a tablet or a spray or a powder or a granule or a liquid or a semisolid. The mouth freshener composition can be in a dosage form selected from the group consisting of, but not limited to, capsules, pills, tablets, mouth dissolving tablet, chewable tablet, effervescent tablet, paste, dried or powdered product for reconstitution with water or other suitable vehicle before use, emulsion, dispersion, oil dispersion, water dispersible granules, micro-emulsion, spray, mouthwash, syrup and the like.

The process involves sifting, individually, the sweetener, diluent and ethyl acetate extract of *Curcuma longa*, hydroalcoholic extract of *Piper longum* and hydroalcoholic extract of *Mentha arvensis* through a sieve having an aperture size of 425 micron. The sweetener is then geometrically mixed with a diluent and then mixed with ethyl acetate extract of *Curcuma longa*, hydroalcoholic extract of *Piper longum* and hydroalcoholic extract of *Mentha arvensis* to form a first homogenised blend. Separately Isopropyl alcohol and purified water are mixed in a predetermined ratio of 90:10 to form a first mixture. At least one binder and at least one preservative are added to the first mixture and dissolved to form a second mixture.

The second mixture is blended with the first blend to form a second blend which is granulated to form granules, followed by drying at a temperature ranging from 40° C. to 70° C. till loss on drying is achieved between 1.5 to 4% followed by sifting, through a sieve having an aperture size of 850 micron, to form dried granules.

The flavouring agents and glidant are then sifted through a sieve (aperture size of 425 micron) to obtain a third mixture. Then the third mixture is mixed with dried and sized granules to form a fourth mixture. Separately the lubricant is sifted through a sieve (aperture size of 250 micron) and mixed with the fourth mixture. This fourth mixture is then compressed to form tablets.

Separately, at least one coating solution is prepared by dissolving at least one pharmaceutically acceptable film forming polymer and at least one pharmaceutically acceptable plasticizer in a pharmaceutically acceptable fluid medium. Finally the tablets are coated with the coating medium to form the mouth freshener composition of the present disclosure.

In another embodiment of the present disclosure, the mouth freshener composition of the present disclosure is in the dosage form of a spray. The process involves adding the ethyl acetate extract of *Curcuma longa*, hydroalcoholic extracts of *Piper longum* and hydroalcoholic extracts of *Mentha arvensis* in an amount ranging from 0.005 to 85.0% to a reaction vessel, followed by mixing to form a homogenised blend. At least one sweetener and at least one flavouring agent are added in an amount ranging from 0.35 to 6.0% to the reaction vessel containing the homogenised blend and mixing to obtain a first homogenised mixture. Solubilizing, the first homogenised mixture in at least one pharmaceutically acceptable fluid medium to form a solubilised mixture. Preparing, at least one pharmaceutically acceptable propellant for oral use. Mixing the solubilised mixture and the pharmaceutically acceptable propellant at low temperature and filling in a container to obtain the mouth freshener composition in the form of a spray.

The term "an effective amount" refers to the amount of the mouth freshener composition of the present disclosure that is required to confer one of the above-described effects on the subject. The effective amount depends on many factors including the indication being treated, the route of administration, the overall condition of the patient, weight of the patient, excipient/s used in the composition and the possibility of co-using with other treatment/s. The dose and dose frequency will vary according to the age, body weight, condition and response of the individual consumer or patient.

In another aspect of the present disclosure, the mouth freshener composition is presented in a pack or dispenser device that comprises one or more unit dosage forms comprising a composition of the present disclosure. The pack may be such that the quality and effectiveness of the packed mouth freshener composition remain unaffected for a long period of time. The pack or dispenser device may be accompanied by instructions for administration.

The present disclosure is further described in light of the following laboratory scale experiments which are set forth for illustration purpose only and not to be construed for limiting the scope of the disclosure. The following experiments can be scaled up to industrial/commercial scale and the results obtained can be extrapolated to industrial/commercial scale.

Experiment No. 1:

Mouth freshener compositions in the form of a tablet was prepared by using the ingredients of the present invention in different appropriate quantities as given in Table-1 and 2. Extracts of *Curcuma longa, Piper longum* and *Mentha arvensis* were commercially purchased from the market as value added products and in an unrecognizable form.

TABLE 1

| Sr. Ingredients in mg/tab | Experiment No. | | | | | | | |
|---|---|---|---|---|---|---|---|---|
| | 1 | 2 | 3 | 4 | 5 | 6 | 7 | 8 |
| 1. Curcuma longa extract | 0.10 | 1.00 | 10.00 | 25.00 | 50.00 | 75.00 | 100.00 | 150.00 |
| 2. Piper longum extract | 0.01 | 0.05 | 0.50 | 1.25 | 2.50 | 3.75 | 5.00 | 7.50 |
| 3. Mentha arvensis extract | 0.01 | 0.05 | 0.50 | 1.25 | 2.50 | 3.75 | 5.00 | 7.50 |
| 4. Mannitol | 219.89 | 218.90 | 209.00 | 192.50 | 165.00 | 137.50 | 110.00 | 55.00 |
| 5. Sucralose | 3.00 | 3.00 | 3.00 | 3.00 | 3.00 | 3.00 | 3.00 | 3.00 |
| 6. Povidone | 5.00 | 5.00 | 5.00 | 5.00 | 5.00 | 5.00 | 5.00 | 5.00 |
| 7. Methylparaben | 0.45 | 0.45 | 0.45 | 0.45 | 0.45 | 0.45 | 0.45 | 0.45 |
| 8. Propylparaben | 0.05 | 0.05 | 0.05 | 0.05 | 0.05 | 0.05 | 0.05 | 0.05 |
| 9. Menthol | 1.50 | 1.50 | 1.50 | 1.50 | 1.50 | 1.50 | 1.50 | 1.50 |
| 10. Peppermint Flavor | 15.00 | 15.00 | 15.00 | 15.00 | 15.00 | 15.00 | 15.00 | 15.00 |
| 11. Anhydrous colloidal silica | 2.50 | 2.50 | 2.50 | 2.50 | 2.50 | 2.50 | 2.50 | 2.50 |
| 12. Magnesium stearate | 2.50 | 2.50 | 2.50 | 2.50 | 2.50 | 2.50 | 2.50 | 2.50 |
| 13. Hydroxypropylmethylcellulose | 2.50 | 2.50 | 2.50 | 2.50 | 2.50 | 2.50 | 2.50 | 2.50 |
| 14. Triacetin | 0.63 | 0.63 | 0.63 | 0.63 | 0.63 | 0.63 | 0.63 | 0.63 |

TABLE 2

| Sr. Ingredients in mg/tab | Experiment No. | | | | | | | | |
|---|---|---|---|---|---|---|---|---|---|
| | 9 | 10 | 11 | 12 | 13 | 14 | 15 | 16 | 17 |
| 1. Harida (Curcuma longa) extract | 200.00 | 300.00 | 400.00 | 500.00 | 600.00 | 700.00 | 800.00 | 850.00 | 900.00 |
| 2. Piper longum extract | 10.00 | 15.00 | 20.00 | 25.00 | 30.00 | 35.00 | 40.00 | 42.50 | 45.00 |
| 3. Mentha arvensis extract | 10.00 | 15.00 | 20.00 | 25.00 | 30.00 | 35.00 | 40.00 | 42.50 | 45.00 |
| 4. Mannitol | 0.00 | 110.00 | 88.00 | 66.00 | 44.00 | 39.60 | 44.00 | 33.00 | 66.00 |
| 5. Sucralose | 3.00 | 6.00 | 7.20 | 8.40 | 9.60 | 10.80 | 12.60 | 13.20 | 14.40 |
| 6. Povidone | 5.00 | 10.00 | 12.00 | 14.00 | 16.00 | 18.00 | 21.00 | 22.00 | 24.00 |
| 7. Methylparaben | 0.45 | 0.90 | 1.08 | 1.26 | 1.44 | 1.26 | 1.89 | 1.98 | 2.16 |
| 8. Propylparaben | 0.05 | 0.10 | 0.12 | 0.14 | 0.16 | 0.14 | 0.21 | 0.22 | 0.24 |
| 9. Menthol | 1.50 | 3.00 | 3.60 | 4.20 | 4.80 | 4.20 | 6.30 | 6.60 | 7.20 |
| 10. Peppermint Flavor | 15.00 | 30.00 | 36.00 | 42.00 | 48.00 | 42.00 | 63.00 | 66.00 | 72.00 |
| 11. Anhydrous colloidal silica | 2.50 | 5.00 | 6.00 | 7.00 | 8.00 | 7.00 | 10.50 | 11.00 | 12.00 |
| 12. Magnesium stearate | 2.50 | 5.00 | 6.00 | 7.00 | 8.00 | 7.00 | 10.50 | 11.00 | 12.00 |
| 13. Hydroxypropylmethylcellulose | 2.50 | 5.00 | 6.00 | 7.00 | 8.00 | 9.00 | 10.50 | 11.00 | 12.00 |
| 14. Triacetin | 0.63 | 1.26 | 1.51 | 1.76 | 2.01 | 2.26 | 2.64 | 2.77 | 3.02 |

The mouth freshener composition contains extracts of Curcuma longa, Piper longum and Mentha arvensis in a homogenized form and the individual portions of the Curcuma longa, Piper longum and Mentha arvensis are value added products appearing in an unrecognizable and physically inseparable form and therefore do not qualify as biological resources under the National Biodiversity Authority (NBA).

Extracts of Curcuma longa, Piper longum, and Mentha arvensis were purchased from various vendors and were tested for identification using High Performance Thin Layer Chromatography, Physical observations etc. Quantification of single chemical moiety was performed using High Performance Liquid Chromatography (HPLC) and group of chemical compounds viz. Tannins, Alkaloids, Polyphenols, Bitters, Flavonoids and Saponins etc. were quantified using various methods such as UV spectrophotometry, Titrimetry, Gravimetry etc. Various quality testing (Ash values, PH, Microbial testing and heavy metal testing) were carried out on extracts of Curcuma longa, Piper longum and Mentha arvensis to check for adulteration.

Experiment 2:
Characterization of the Mouth Freshener Composition
Testing of Anti-Microbial and Anti-Fungal Activity of the Mouth Freshener Composition
Procedure:
The anti-microbial activity and the anti-fungal activity of the mouth freshener composition of the present disclosure was determined by testing it on Escherichia coli, Staphylococcus aureus and Candida albicans as the test microorganisms in comparison with a product presently available in the market (herein forward referred to as Product X), methanol and a standard drug i.e. Chlorhexidine. Escherichia coli, Staphylococcus aureus were grown in Luria-Bertani broth (LB broth) and Candida albicans was grown in Potato Dextrose broth (PD broth) until the growth reached approximately $10^6$ cfu (colony forming units) per ml culture was attained. 100 µl of this culture was used for the antimicrobial assay.

The 1-4% solution of powder extract was prepared by dissolving the extract in methanol as a solvent and all these solutions were store at 4° C. temperature till further use.

Inoculation of Test Plates:
Mueller-Hinton (HiMedia) agar plates were used to carry out the testing of the anti-microbial activity and Potato dextrose (Himedia) agar plates were used to carry out the testing of the anti-fungal activity of the mouth freshener composition. The dried surface of a Mueller-Hinton agar plate was inoculated by spreading 100 µl culture suspension on the agar surface. Wells were bored into the surface of the inoculated agar plate using a sterile cork borer having 8 mm diameter and 100 µl of the mouth freshener composition, the marketed product, methanol and standard chlorhexidine was added to the wells in triplicates. The inoculated plates were kept in refrigerator for pre-diffusion for 30 minutes and then placed in an incubator maintained at 37° C. for 24 hours and at 30° C. for 24 hours for the fungus.

The marketed product, methanol and standard chlorhexidine were used as controls and the mouth freshener composition (55 mg active ingredient per tablet) was dissolved in methanol to obtain different concentrations (1% to 4%) of the test and used in the present study.

Results:

The antibacterial activity and the anti-fungal activity of the mouth freshener composition is summarised in Table 3.

TABLE 3

Anti-microbial the anti-fungal activity of different concentrations of the mouth freshener composition against *Escherichia coli*, *Staphylococcus aureus* and *Candida albicans*.

| Name of the organism | Mouth freshener composition of the present disclosure | | | | Product X | Methanol | Chlorhexidine |
|---|---|---|---|---|---|---|---|
| | 1% | 2% | 3% | 4% | | | |
| *Escherichia coli* | 14 | 16 | 23 | 25 | 00 | 11 | 15 |
| *Staphylococcus aureus* | 16 | 25 | 25 | 25 | 00 | 11 | 18 |
| *Candida albicans* | 20 | 25 | 25 | 25 | 00 | 11 | 19 |

Table-3 discloses that 2%, 3% and 4% concentrations of the mouth freshener composition showed a greater zone of inhibition, of 25 mm each, against *Staphylococcus aureus* than Methanol (11 mm) and standard drug Chlorhexidine (18 mm). The 1% concentration of the mouth freshener composition tablet showed more zone of inhibition (of 16 mm) against *Staphylococcus aureus* than Methanol (11 mm) and marketed product (0 mm).

Also, the 3% and 4% concentrations of the mouth freshener composition showed more zone of inhibition (of 23 mm and 25 mm respectively) against *E. coli* than Methanol (11 mm) and standard drug Chlorhexidine (15 mm). The 2% and 3% concentrations of the mouth freshener composition showed more zone of inhibition (of 14 mm & 16 mm respectively) against *E. coli* than Methanol (11 mm) and marketed product (0 mm).

The mouth freshener composition was active against *Candida albicans* even at a lower concentration of 1% showing a significant zone of inhibition of 20 mm as compared to the standard drug Chorhexidine (19 mm). All concentrations of the mouth freshener composition i.e. concentration of 1%, 2%, 3% and 4% showed more zone of inhibition (of 20 mm, 25 mm, 25 mm, and 25 mm, respectively) against *Candida albicans* than Methanol (11 mm) and standard drug Chlorhexidine (19 mm) and marketed product (0 mm).

The Product X did not show any anti-microbial or any anti-fungal activity.

The results conclude that the mouth freshener composition of the present disclosure possesses anti-microbial and anti-fungal activity.

Experiment 3:

Experiments were conducted to determine the stability of various batches of the mouth freshener composition of the present disclosure. The results are tabulated in tables 4-7.

Stability Study (Physical Data):

Batch No: AHPL/AYTAB/1514/011, Packing: High-density polyethylene (HDPE)

TABLE 4

| | | Condition | | | | | |
|---|---|---|---|---|---|---|---|
| | | 1M | 2M | 3M | | 6M | |
| Parameters | Initial | 40° C./75% RH | 40° C./75% RH | 30° C./65% RH | 40° C./75% RH | 30° C./65% RH | 40° C./75% RH |
| Description | Yellow colored tablet with occasional reddish to black flecks, oval shaped plain on one side and embossed 'ā' on other side, film coated tablet | Complies | Complies | Complies | Complies | Complies | Complies |
| Thickness(mm) | 4.00-4.10 | 3.97-4.00 | 3.97-4.00 | 3.90-4.00 | 3.90-4.00 | 3.90-4.00 | 3.90-4.10 |
| LOD(%) | 3.23 | 3.28 | 3.60 | 2.80 | 2.73 | 3.60 | 3.20 |

CONCLUSION: From the above stability data it is observed that there is no change in thickness of tablet during stability study and only about ±1% variation in Loss on drying (LOD) were observed during the span of 6 months. The tablet was stable in High-density polyethylene (HDPE) packing and does not require any special storage conditions.

Batch No: AHPL/AYTAB/1514/011, Packing: Polyvinylidene chloride (PVDC)

TABLE 5

| | | Condition | | | | | |
|---|---|---|---|---|---|---|---|
| | | 1M | 2M | 3M | | 6M | |
| Parameters | Initial | 40° C./75% RH | 40° C./75% RH | 30° C./65% RH | 40° C./75% RH | 30° C./65% RH | 40° C./75% RH |
| Description | Yellow colored tablet with occasional reddish to black flecks, oval shaped plain on one side and embossed 'ā' on other side, film coated tablet | Complies | Complies | Complies | Complies | Slight change in color | Slight change in color |

TABLE 5-continued

|  |  | 1M | 2M | 3M | | 6M | |
|---|---|---|---|---|---|---|---|
| Parameters | Initial | 40° C./75% RH | 40° C./75% RH | 30° C./65% RH | 40° C./75% RH | 30° C./65% RH | 40° C./75% RH |
| Thickness(mm) | 4.00-4.10 | 4.00-4.10 | 4.05-4.08 | 3.93-3.99 | 3.90-4.00 | 3.95-3.99 | 4.00-4.10 |
| LOD(%) | 3.23 | 4.12 | 4.90 | 3.43 | 3.91 | 3.78 | 3.23 |

CONCLUSION: From the above stability data it is observed that there is no change in thickness of tablet during stability study and only about 3% variations in Loss on drying (LOD) with slight change in color were observed during the span of 6 months. The tablet was stable and required low humidity storage conditions to remain physically unchanged. Hence, the storage conditions for the product in Polyvinylidene chloride (PVDC) packing is recommended as "Store in cool, dry place away from direct sunlight"

Stability Study (Chemical Data):
Batch No: AHPL/AYTAB/1514/011, Packing: High-density polyethylene (HDPE)

TABLE 6

|  |  |  | 1M | 2M | 3M | | 6M | |
|---|---|---|---|---|---|---|---|---|
| Parameters | Limits | Initial | 40° C./75% RH | 40° C./75% RH | 30° C./65% RH | 40° C./75% RH | 30° C./65% RH | 40° C./75% RH |
| identification by HPTLC | The principal band of Curcumin should be observed at Rf 0.45 (±0.1) | Complies | Complies | Complies | Complies | Complies | Complies | Complies |
| Assay of Total Curcuminoids (% w/w) | NLT 4.00 | 6.91 | 7.17 | 6.90. | 6.74 | 6.86 | 5.73 | 5.99 |
| Microorganism tested | | | | | | | | |
| Total aerobic microbial count (cfu/g) | NMT 1000 | Complies | Not Applicable | | Complies | Complies | Complies | Complies |
| Total combined yeast/moulds count (cfu/g) | NMT 100 | Complies | | | Complies | Complies | Complies | Complies |
| Escherichia coli | Absent | Complies | | | Complies | Complies | Complies | Complies |
| Salmonella | Absent | Complies | | | Complies | Complies | Complies | Complies |
| Pseudomonas aeruginosa | Absent | Complies | | | Complies | Complies | Complies | Complies |
| Staphylococcus aureus | Absent | Complies | | | Complies | Complies | Complies | Complies |
| Heavy metal tested | | | | | | | | |
| Arsenic | NMT 5.0 | Complies | | Not Applicable | | | | |
| Cadmium | NMT 1.0 | Complies | | | | | | |
| Lead | NMT 10.0 | Complies | | | | | | |
| Mercury | NMT 1.0 | Complies | | | | | | |

CONCLUSION: From the above stability data it is observed that assay of the composition of the present disclosure during stability study of six months was found to be within specified limits. There was no microbial growth observed at the end of 6 months study. Thus, it can be concluded that the composition of the present disclosure is chemically stable.

Batch No: AHPL/AYTAB/1514/011, Packing: PVDC

TABLE 7

|  |  |  | 1M | 2M | 3M | | 6M | |
|---|---|---|---|---|---|---|---|---|
| Parameters | Limits | Initial | 40° C./75% RH | 40° C./75% RH | 30° C./65% RH | 40° C./75% RH | 30° C./65% RH | 40° C./75% RH |
| identification by HPTLC | The principal band of curcumin should be observed at Rf 0.45 (±0.1) | Complies | Complies | Complies | Complies | Complies | Complies | Complies |
| Assay of Total Curcuminoids (% w/w) | NLT 4.00 | 6.91 | 7.05 | 6.86 | 7.14 | 7.16 | 5.84 | 5.63 |
| Microorganism tested | | | | | | | | |
| Total aerobic microbial count (cfu/g) | NMT 1000 | Complies | Not Applicable | | Complies | Complies | Complies | Complies |
| Total combined yeast/moulds count (cfu/g) | NMT 100 | Complies | | | Complies | Complies | Complies | Complies |

TABLE 7-continued

| | | | Condition | | | | | |
|---|---|---|---|---|---|---|---|---|
| | | | 1M | 2M | 3M | | 6M | |
| Parameters | Limits | Initial | 40° C./ 75% RH | 40° C./ 75% RH | 30° C./ 65% RH | 40° C./ 75% RH | 30° C./ 65% RH | 40° C./ 75% RH |
| Escherichia coli | Absent | Complies | | | Complies | Complies | Complies | Complies |
| Salmonella | Absent | Complies | | | Complies | Complies | Complies | Complies |
| Pseudomonas aeruginosa | Absent | Complies | | | Complies | Complies | Complies | Complies |
| Staphylococcus aureus | Absent | Complies | | | Complies | Complies | Complies | Complies |
| Heavy metal tested | | | | | | | | |
| Arsenic | NMT 5.0 | Complies | | | Not Applicable | | | |
| Cadmium | NMT 1.0 | Complies | | | | | | |
| Lead | NMT 10.0 | Complies | | | | | | |
| Mercury | NMT 1.0 | Complies | | | | | | |

CONCLUSION: From the above stability data it is observed that Assay of the composition of the present disclosure during stability study of six months was found to be within specified limits in PVDC packing. Also microbial limit and heavy metals were within limits. Hence, it can be concluded that the composition of the present disclosure is chemically stable in PVDC packing.

Overall Conclusion:

The composition of the present disclosure was physically stable in HDPE container and PVDC packing. Though there is a slight change in color in PVDC packing at the end of 6 months study, the product was chemically stable. Also no microbial growth was found at the end of 6 months study in both HDPE container and PVDC packing. Hence the composition of the present disclosure is stable in HDPE container and PVDC packing. The storage condition for the composition of the present disclosure in PVDC packing is recommended as "Store in cool, dry place away from direct sunlight"

Experiment—4

Evaluation of Efficacy and Safety of the Mouth Freshener Composition in Patients Suffering from Halitosis:

(CTRI No: CTRI/2015/07/006058, Registered on: 31 Jul. 2015)

54 male and female subjects, between 18-54 years, suffering from moderate to severe halitosis (analyzed using Bad Breath Analyzer) were selected for the study. Six subjects, out of 54 subjects did not meet the inclusion/exclusion criteria, hence were not included in the study. Subject's general, systemic and oral examinations were done. Subject was asked for history of any concomitant medical illness/ medications or any incidence of infection, duration and severity of infection during last 6 months. Subject was asked for the use of antibiotic, antimicrobial or analgesic medications, anti-inflammatory drugs, mouthwash, mouth fresheners (lozenges/tablets) or desensitizing toothpaste during last 1 month from screening visit.

The halitosis (bad breath) was also measured using organoleptic assessment scale as 0=no appreciable odour, 1=barely noticeable odour, 2=slight but clearly noticeable odour, 3=moderate odour, 4=strong odour and 5=extremely foul odour. Also halitosis (bad breath) was measured using bad breath analyzer on graded scale as 0=no halitosis, 1=mild halitosis, 2=moderate halitosis and 3=severe halitosis.

Out of 48 recruited subjects, 47 subjects completed the study, while 1 subject dropped out prematurely. All study subjects were received 2 tablets of the mouth freshener composition four times a day (i.e. 2 tablets after breakfast, 2 tablets after lunch, 2 tablets after evening tea time/snacks and 2 tablets after dinner) orally for 60 days.

All study subjects were advised to keep 2 tablets of the mouth freshener composition on the tongue & suck on the tablet till it dissolves completely in the mouth. The mouth freshener composition's dosage was adjusted from minimum 1 tablet twice a day to maximum 2 tablets 4 times a day as per the patient's tolerance. From day 60 onwards till day 75, all study subjects were advised not to use the mouth freshener composition and come to follow up on day 75 (last study visit) to observe any relapse/recurrence of halitosis.

At the end of the treatment period (60 days), statistically significant improvement was observed in halitosis assessed using Bad Breath analyzer and on organoleptic scale. At the end of treatment, statistically significant improvement was observed in gingivitis assessed on Loe and Silness Gingival Index. Also at the end of treatment, statistically significant improvement was observed in plaque assessed on Turesky modification of Quigley Hein Index.

Some patients had seasonal mild sore throat and mild cough (during study period), which were resolved with the mouth freshener composition. Patient did not require additional treatment other than the mouth freshener composition, indicating benefits of the mouth freshener composition on symptoms such as sore throat and cough.

Even after taking two months of continuous treatment with the mouth freshener composition not a single patient reported staining of teeth. Feeling of wellbeing and slight improvement in quality of life was observed in subjects at the end of the study treatment.

It was observed from the data that not a single subject reported unacceptability of taste of the mouth freshener composition. Initially, only 1 subject reported burning sensation and dryness of mouth after usage of the mouth freshener composition, but subject did not stop usage of the mouth freshener composition and the problem was resolved without any additional treatment. At the end of the treatment period, no subject reported burning sensation and dryness of mouth after usage of study drug.

On day 60, global evaluation for overall improvement was done by physician and by patient. According to global evaluation for overall improvement done by physician and by patient, excellent improvement was observed in 44 (95.7%) subjects and good improvement was observed in 2 (4.3%) subjects. The results are tabulated in Table 8.

TABLE 8

| | Global assessment of drug's tolerability | | | |
|---|---|---|---|---|
| | assessed by physician on day 60 | | assessed by patient on day 60 | |
| Assessment | No. of Cases # (N = 46) | Percentage (%) | No. of Cases # (N = 46) | Percentage (%) |
| Excellent Tolerability | 41 | 89.1 | 41 | 89.1 |
| Good Tolerability | 05 | 10.9 | 05 | 10.9 |
| Fair Tolerability | — | — | — | — |
| Poor Tolerability | — | — | — | — |

It can be concluded from the results of the study that the mouth freshener composition of the present disclosure is safe and effective in alleviating halitosis, gingivitis and plaque. Even after stoppage of treatment for 15 days, there was no relapse in halitosis. the mouth freshener composition is also effective in treating sore throat, cough and common cold. Since the mouth freshener composition contains *Curcuma longa*, as main active ingredient, long term usage of the mouth freshener composition may help in improving quality of life.

TECHNICAL ADVANCEMENTS

The present disclosure described herein above has several technical advantages including, but not limited to, the realization of:

- a mouth freshener composition which has a quick onset of action;
- a mouth freshener composition for alleviating the symptoms of common cold, sore throat, cough and bronchitis;
- a mouth freshener which can also be used as a rejuvenator and as an immunomodulator; and
- a process for producing a mouth freshener composition which is devoid of any severe side effects.

The embodiments as described herein above, and various features and advantageous details thereof are explained with reference to the non-limiting embodiments in the description. Descriptions of well-known aspects, components and molecular biology techniques are omitted so as to not unnecessarily obscure the embodiments herein.

The foregoing description of specific embodiments so fully reveal the general nature of the embodiments herein, that others can, by applying current knowledge, readily modify and/or adapt for various applications of such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein. Further, it is to be distinctly understood that the foregoing descriptive matter is to be interpreted merely as illustrative of the disclosure and not as a limitation.

Having described and illustrated the principles of the present disclosure with reference to the described embodiments, it will be recognized that the described embodiments can be modified in arrangement and detail without departing from the scope of such principles.

While considerable emphasis has been placed herein on the particular features of this disclosure, it will be appreciated that various modifications can be made, and that many changes can be made in the preferred embodiment without departing from the principles of the disclosure. These and other modifications in the nature of the disclosure or the preferred embodiments will be apparent to those skilled in the art from the disclosure herein, whereby it is to be distinctly understood that the foregoing descriptive matter is to be interpreted merely as illustrative of the disclosure and not as a limitation.

The invention claimed is:

1. An antimicrobial mouth freshener composition comprising:
    i) ethyl acetate extract of *Curcuma longa* in an amount ranging from 0.05 to 85.0% with respect to the total weight of the composition;
        wherein said extract of *Curcuma longa* has at least 5% of curcuminoids;
    ii) hydroalcoholic extract of *Piper longum* in an amount ranging from 0.005 to 5.0% with respect to the total weight of the composition;
        wherein said extract of *Piper longum* has at least 1% of piperine;
    iii) hydroalcoholic extract of *Mentha arvensis* in an amount ranging from 0.005 to 5.0% with respect to the total weight of the composition;
        wherein said extract of *Mentha arvensis* has at least 0.5% of total volatile oil;
    iv) at least one diluent selected from the group consisting of mannitol, sucralose, lactose, microcrystalline cellulose, dextrin, maltitol and isomalt in an amount ranging from 0.1 to 90% with respect to the total weight of the composition;
    v) at least one sweetener selected from the group consisting of sucralose, acesulfame potassium, neotame, saccharine sodium, sucrose, aspartame *stevia* extracts, steviol glycoside and any sweetener derived from *stevia* plant in an amount ranging from 1.0 to 2.0% with respect to the total weight of the composition;
    vi) at least one binder selected from the group consisting of povidone, hydroxymethylcellulose, ethylcellulose, hydroxypropyl cellulose, starch, gum acacia, alginate, and carboxymethyl cellulose sodium and carboxymethyl cellulose calcium in an amount ranging from 1.5 to 3.0% with respect to the total weight of the composition;
    vii) at least one preservative selected from the group consisting of methylparaben, propylparaben, ethyl paraben, butyl paraben and sodium benzoate in an amount ranging from 0.015 to 0.30% with respect to the total weight of the composition;
    viii) a pharmaceutically acceptable fluid medium selected from the group consisting of dichloromethane and isopropyl alcohol in a ratio of 90:10;
    ix) at least one pharmaceutically acceptable flavouring agent selected from the group consisting of menthol, peppermint, lemon, fennel, honey, mix fruit, orange, pineapple, raspberry, strawberry, vanilla, chocolate and cardamom in an amount ranging from 0.35 to 6.0% with respect to the total weight of the composition;
    x) at least one pharmaceutically acceptable lubricant selected from the group consisting of magnesium stearate, calcium stearate, stearic acid, glyceryl palmitostearate, colloidal anhydrous silica, sodium stearylfumarate and glyceryl monostearate in an amount ranging from 0.50 to 1.20% with respect to the total weight of the composition;

xi) at least one pharmaceutically acceptable glidant consisting of colloidal anhydrous silica in an amount ranging from 0.50 to 1.20% with respect to the total weight of the composition;

xii) at least one pharmaceutically acceptable film forming agent selected from the group consisting of hydroxylpropyl methylcellulose, ethylcellulose, hydroxylpropyl cellulose, povidone and polyvinyl alcohol in an amount ranging from 0.8 to 1.2% with respect to the total weight of the composition; and xiii) at least one pharmaceutically acceptable plasticizer agent selected from the group consisting of but not limited to triacetin, glycerin, propylene glycol, polyethylene glycol and tweens in an amount ranging from 0.2 to 0.3% with respect to the total weight of the composition, wherein a ratio of extracts of said *Curcuma longa* to said *Piper longum* to said *Mentha arvensis* is 20:1:1.

2. The composition as claimed in claim 1, wherein the excipient comprises a mixture of mannitol, sucralose, povidone, methylparaben, propylparaben, menthol, peppermint flavour, anhydrous colloidal silica, magnesium stearate, hydroxylpropylmethylcellulose and triacetin.

3. The composition as claimed in claim 2, wherein said composition further comprises at least one pharmaceutically acceptable disintegrant selected from the group consisting of crospovidone, croscarmellose sodium, sodium starch glycolate, starch and colloidal anhydrous silica in an amount ranging from 4.0 to 6.0% with respect to the total weight of the composition.

4. The composition as claimed in claim 1, wherein said composition comprises:

i) ethyl acetate extract of *Curcuma longa* in an amount ranging from 0.05 to 85.0% with respect to the total weight of the composition;
    wherein said extract of *Curcuma longa* has at least 5% of curcuminoids;

ii) hydroalcoholic extract of *Piper longum* in an amount ranging from 0.005 to 5.0% with respect to the total weight of the composition;
    wherein said extract of *Piper longum* has at least 1% of piperine;

iii) hydroalcoholic extract of *Mentha arvensis* in an amount ranging from 0.005 to 5.0% with respect to the total weight of the composition;
    wherein said extract of *Mentha arvensis* has at least 0.5% of total volatile oil;

iv) mannitol as a diluent in an amount ranging from 0.1 to 90% with respect to the total weight of the composition;

v) sucralose as a sweetener in an amount ranging from 1.0 to 2.0% with respect to the total weight of the composition;

vi) povidone as a binder in an amount ranging from 1.5 to 3.0% with respect to the total weight of the composition;

vii) at least one preservative selected from methylparaben and propylparaben in an amount ranging from 0.015 to 0.30% with respect to the total weight of the composition;

viii) a pharmaceutically acceptable fluid medium selected from the group consisting of dichloromethane and isopropyl alcohol in a ratio of 90:10;

ix) at least one pharmaceutically acceptable flavouring agent selected from menthol, peppermint in an amount ranging from 0.35 to 6.0% with respect to the total weight of the composition;

x) magnesium stearate as a pharmaceutically acceptable lubricant in an amount ranging from 0.50 to 1.20% with respect to the total weight of the composition;

xi) colloidal anhydrous silica as a pharmaceutically acceptable glidant consisting of in an amount ranging from 0.50 to 1.20% with respect to the total weight of the composition;

xii) hydroxylpropylmethylcellulose as a pharmaceutically acceptable film forming agent in an amount ranging from 0.8 to 1.2% with respect to the total weight of the composition; and xiii) triacetin pharmaceutically acceptable plasticizer agent in an amount ranging from 0.2 to 0.3% with respect to the total weight of the composition.

5. The composition as claimed in claim 1, wherein said composition is orally administered in a dosage form selected from tablets and spray.

6. The composition as claimed in claim 5, wherein said tablets are stable up to at least 6 months when stored in HDPE and PVDC packing.

7. The composition as claimed in claim 1, wherein the size of zone inhibition of said composition is in the range of 20 to 25 mm when 3-4 wt. % of said composition is dissolved in methanol.

8. The composition as claimed in claim 1, wherein said composition is used for alleviating the symptoms of common cold, sore throat, cough and Bronchitis.

9. The composition as claimed in claim 1, wherein said composition is used as a rejuvenator and as an immunomodulator.

10. The composition as claimed in claim 1, wherein said composition is used for the treatment of halitosis.

* * * * *